(12) United States Patent
Hing et al.

(10) Patent No.: US 8,613,876 B2
(45) Date of Patent: Dec. 24, 2013

(54) FOAMED CERAMICS

(75) Inventors: Karin Angela Hing, London (GB); William Bonfield, Hertfordshire (GB)

(73) Assignee: ApaTech Limited (GB)

( * ) Notice: Subject to any disclaimer, the term of this patent is extended or adjusted under 35 U.S.C. 154(b) by 385 days.

(21) Appl. No.: 12/216,710

(22) Filed: Jul. 9, 2008

(65) Prior Publication Data
US 2009/0162414 A1  Jun. 25, 2009

Related U.S. Application Data

(63) Continuation of application No. 09/787,922, filed as application No. PCT/GB99/03283 on Oct. 5, 1999, now abandoned.

(30) Foreign Application Priority Data

Oct. 5, 1998 (GB) .................................. 9821663.3

(51) Int. Cl.
*C04B 35/622* (2006.01)

(52) U.S. Cl.
USPC ................ 264/128; 264/129; 264/42; 264/43

(58) Field of Classification Search
USPC ...................... 264/128, 129, 42, 43
See application file for complete search history.

(56) References Cited

U.S. PATENT DOCUMENTS

| 4,158,684 A | | 6/1979 | Klawitter et al. | |
|---|---|---|---|---|
| 5,043,118 A | * | 8/1991 | Kim et al. | 264/641 |
| 5,266,248 A | | 11/1993 | Ohtsuka et al. | |
| 5,458,837 A | | 10/1995 | Roberts et al. | |
| 5,656,217 A | * | 8/1997 | Rogers et al. | 264/640 |
| 5,656,562 A | * | 8/1997 | Wu | 264/122 |
| 5,665,127 A | * | 9/1997 | Moltgen et al. | 51/293 |
| 5,728,395 A | | 3/1998 | Ohtsuka et al. | |
| 5,769,897 A | | 6/1998 | Harle | |
| 5,895,897 A | * | 4/1999 | Sasaki | 181/286 |

FOREIGN PATENT DOCUMENTS

| EP | 0360244 A1 | 3/1990 |
|---|---|---|
| EP | 0767154 A1 | 9/1997 |
| EP | 0851402 A | 7/1998 |
| GB | 2317887 A | 4/1998 |
| JP | 53063409 A | 6/1978 |
| WO | 9304013 A | 3/1993 |
| WO | WO93/04013 * | 3/1993 |
| WO | 9744292 | 11/1997 |

OTHER PUBLICATIONS

Fischer, E.K., "Colloidal Dispersions," (1951), pp. 304-305, John Wiley & Sons, NY.

* cited by examiner

*Primary Examiner* — John Hoffman
(74) *Attorney, Agent, or Firm* — Bacon & Thomas, PLLC

(57) ABSTRACT

A method for the production of a macroporous ceramic foam, wherein: (a) forming a ceramic slip comprising a substantially homogeneous mixture of a ceramic particulate, an organic binder in a liquid carrier, and optionally one or more surfactants, wherein at least one surfactant is present if the organic binder does not function as a surfactant, and wherein the ceramic slip preferably has a viscosity in the range of from 15 to 200 mPas$^{-1}$; (b) foaming the ceramic slip; and (c) heating the foamed ceramic slip at a temperature sufficient to substantially burn out the organic binder. The macroporous ceramic foam is suitable for use in biomedical applications such as synthetic bones, tissue engineering scaffolds or drug delivery devices.

31 Claims, 5 Drawing Sheets

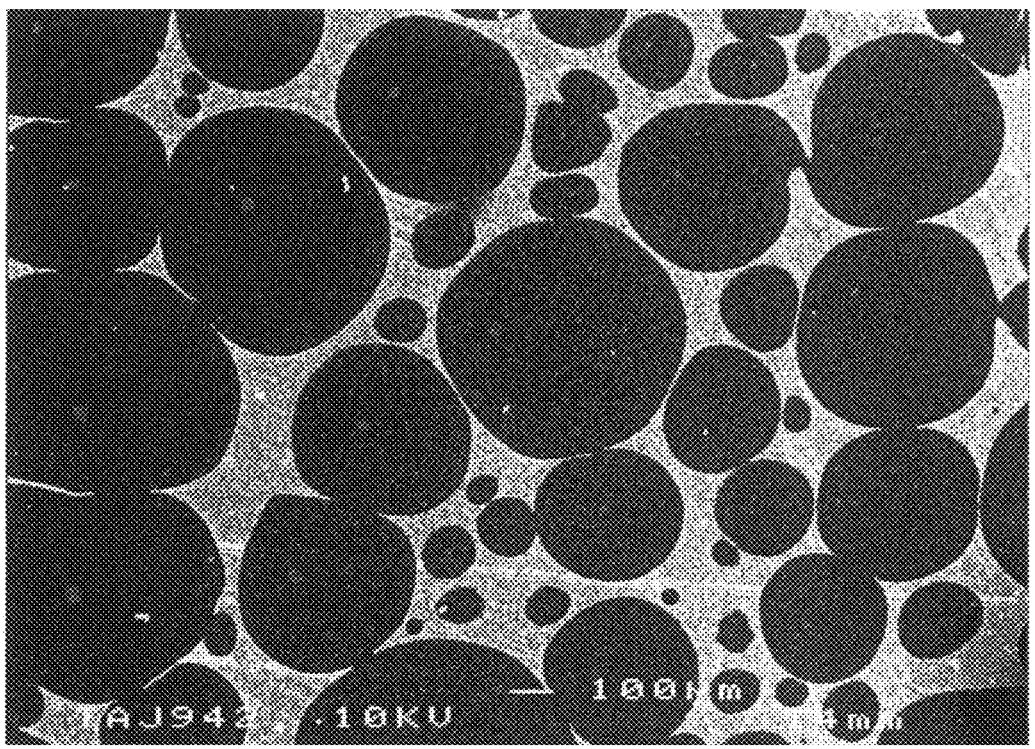
Figure 1 (Ref. TAJ942).
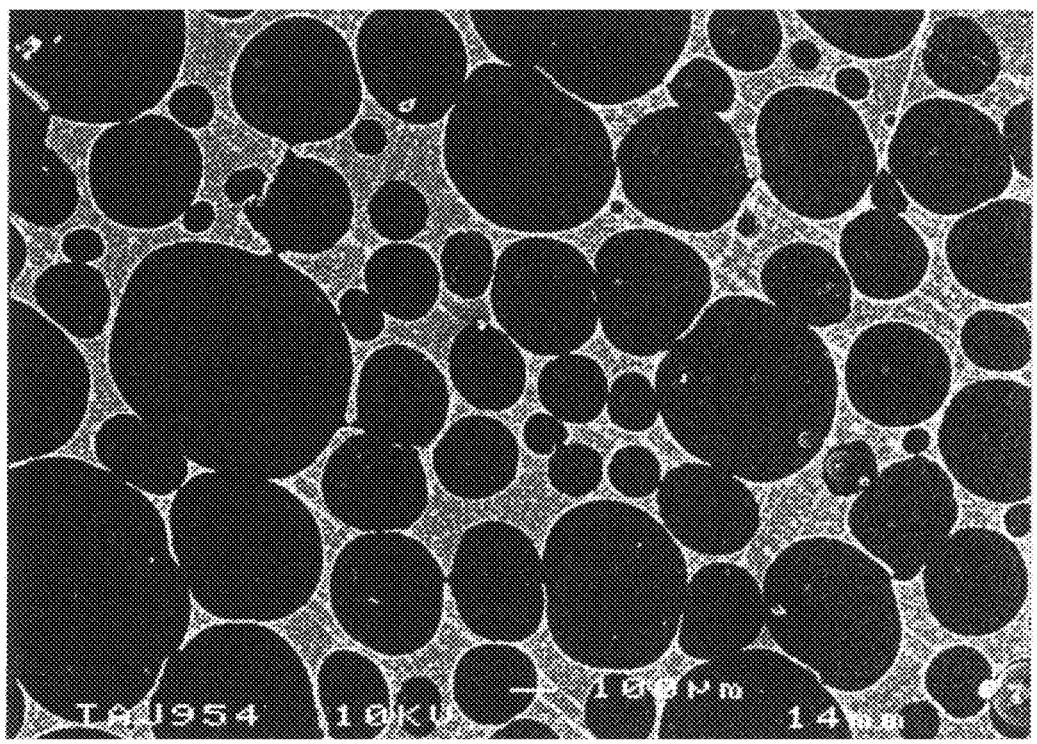
Figure 2 (Ref. TAJ954).

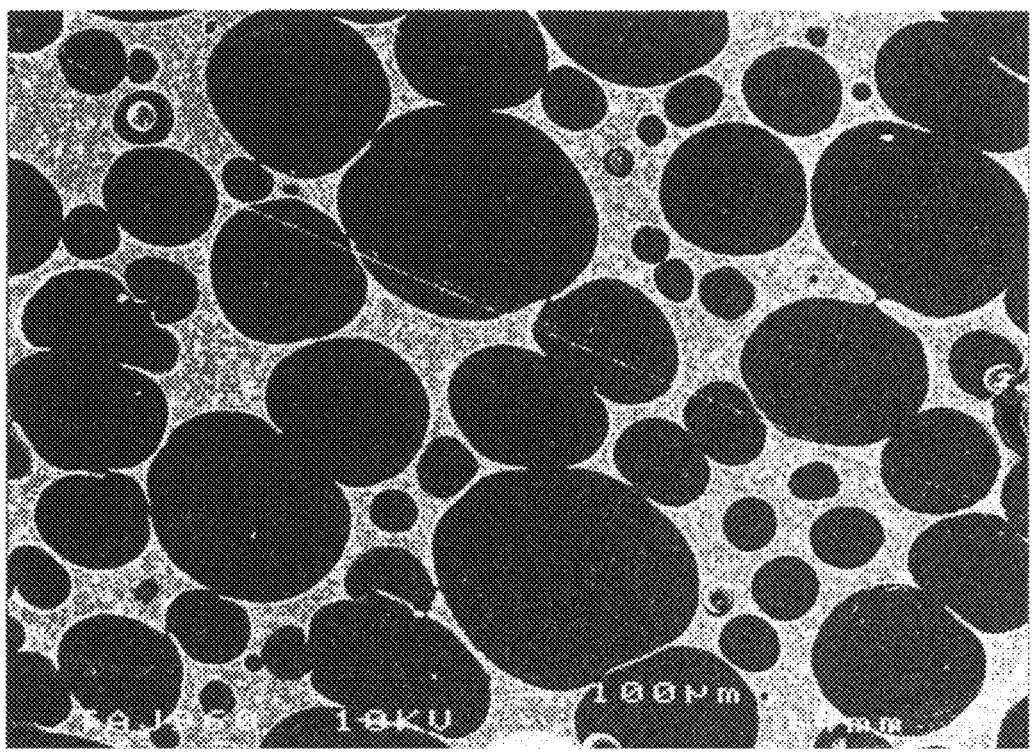
Figure 3 (Ref: TAJ960).
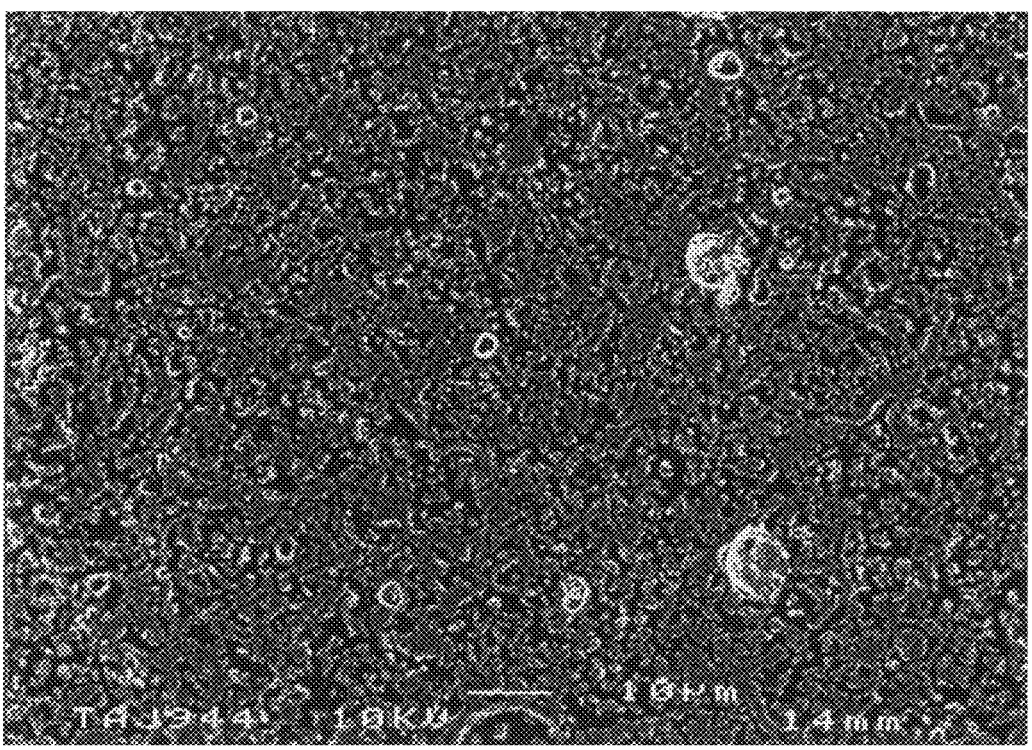
Figure 4 (Ref: TAJ944).

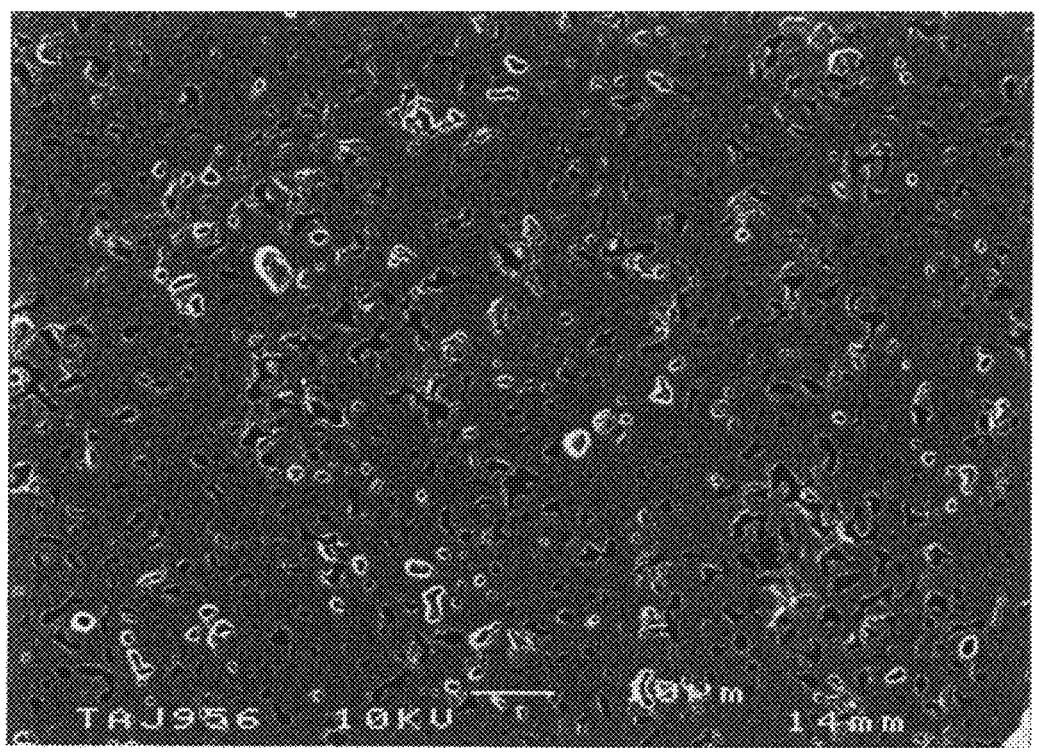
Figure 5 (Ref: TAJ956).
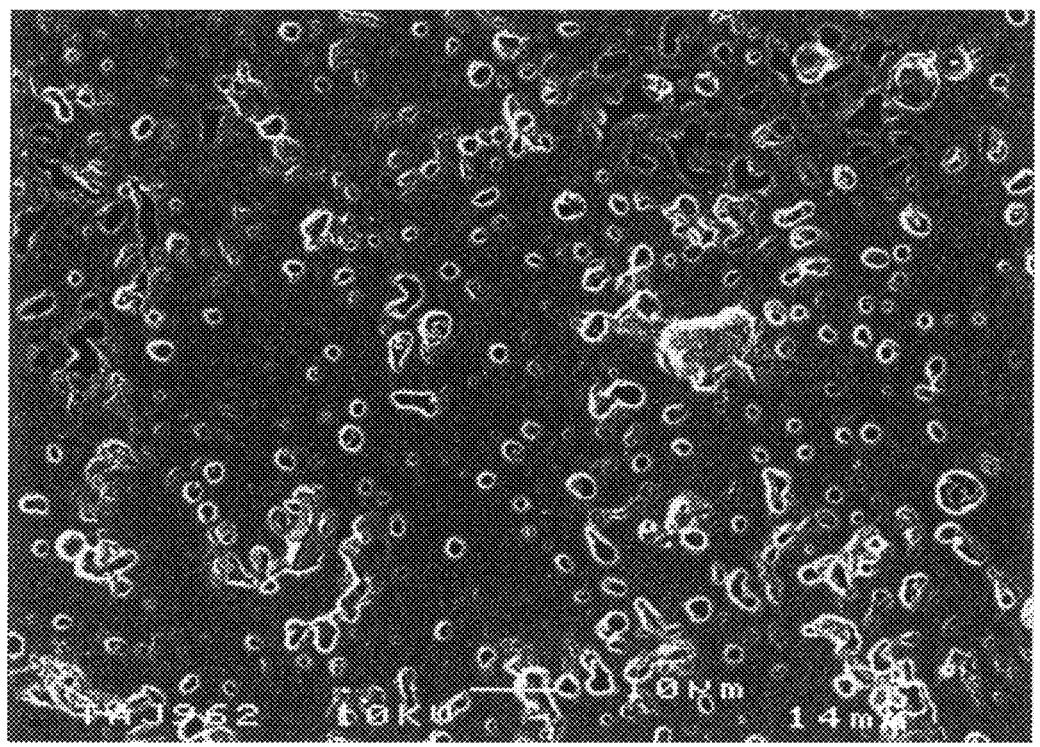
Figure 6 (Ref: TAJ962).

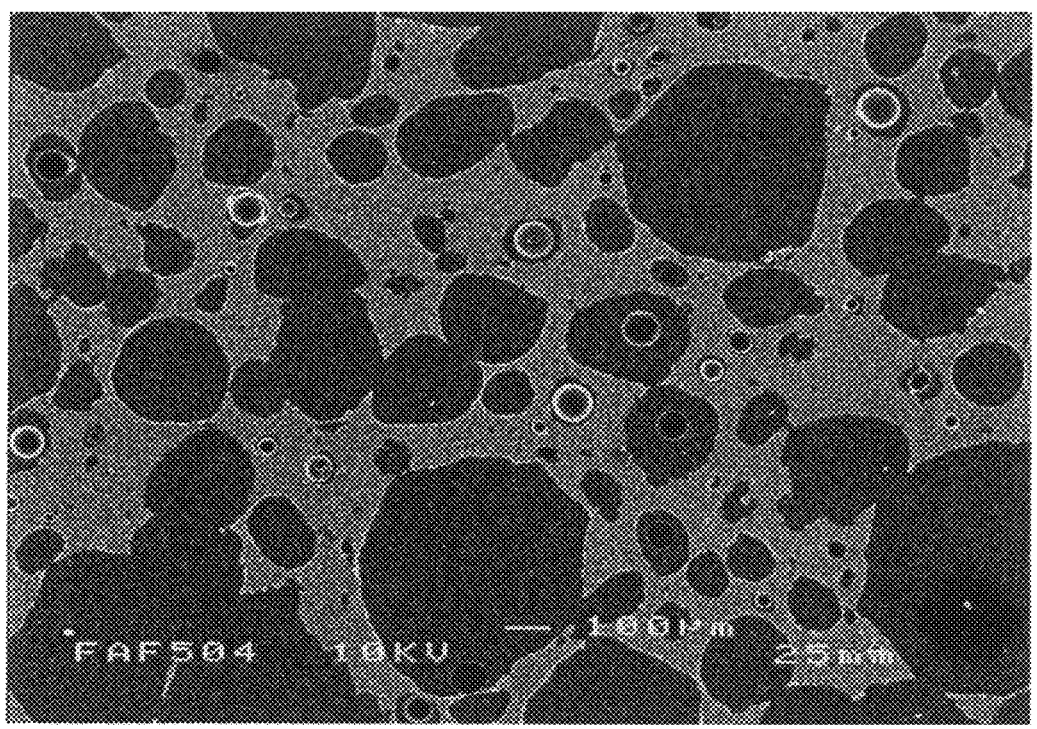
Figure 7 (Ref: FAF504).
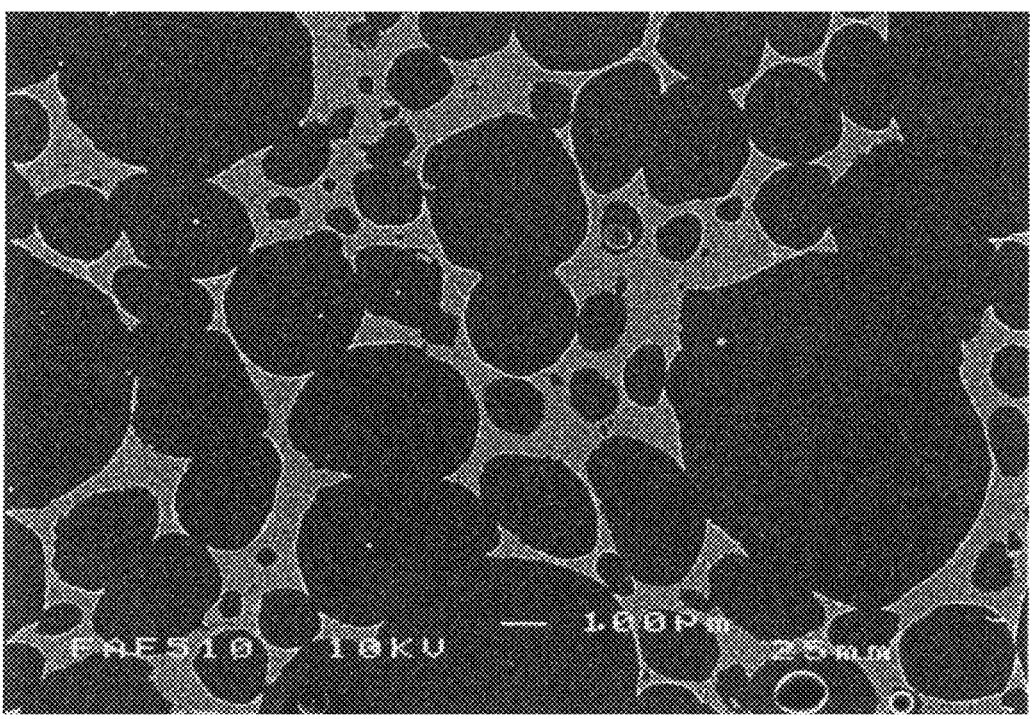
Figure 8 (Ref: FAF510).

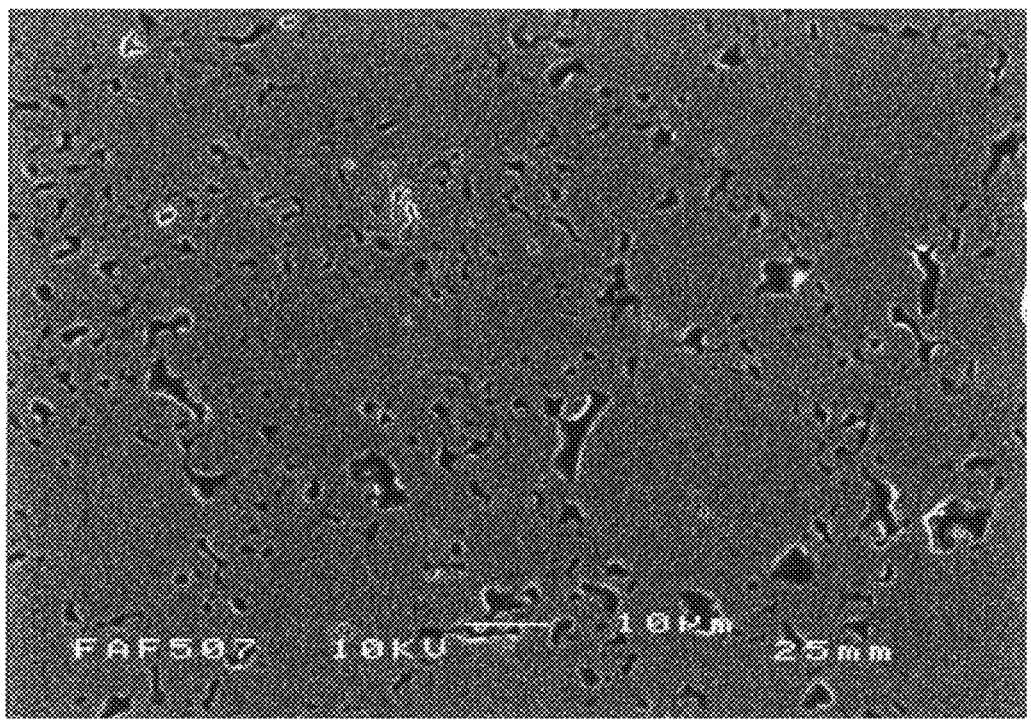
Figure 9 (Ref: FAF507).
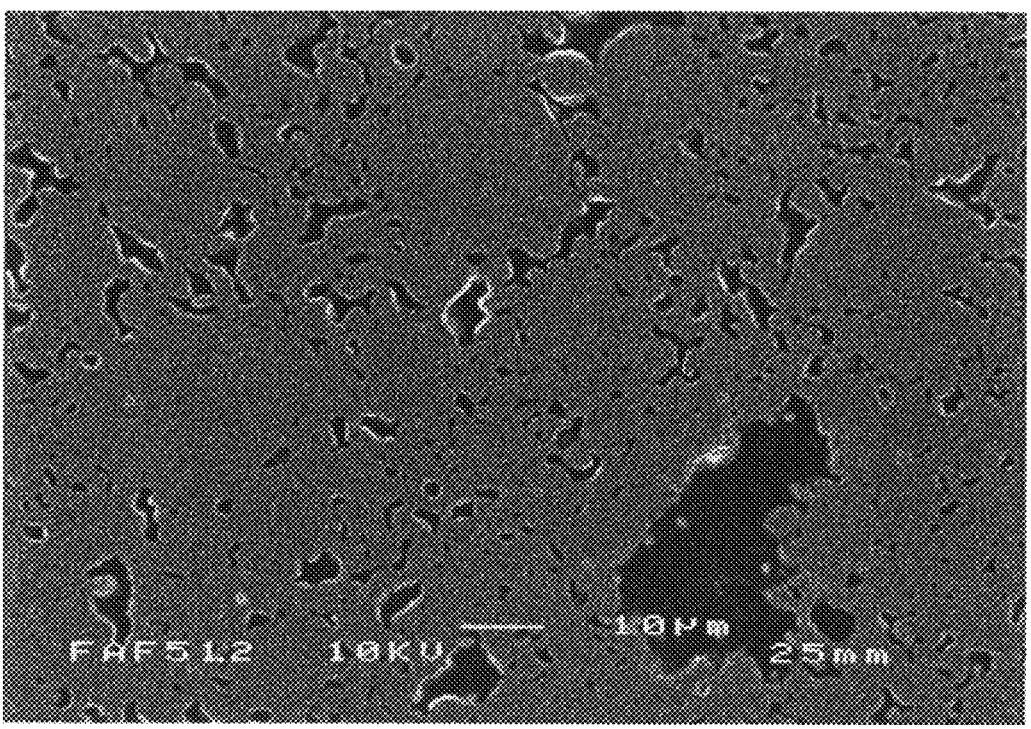
Figure 10 (Ref: FAF512).

FOAMED CERAMICS

This application is a continuation application of pending U.S. application Ser. No. 09/787,922, filed on Jun. 13, 2001, (of which the entire disclosure of the pending, prior application is hereby incorporated by reference), which is a 371 of PCT/GB99/03283, filed Oct. 5, 1999.

The present invention relates to a method for producing foamed ceramic materials and, in particular, foamed ceramic materials which are suitable for use in biomedical applications.

The replacement of old, damaged or diseased bone is now an established procedure and an estimated 40,000 hip replacements are performed annually within Britain alone, of which 18% are revisions. As surgical technique and medical knowledge continue to advance, there is a growth in the demand for synthetic bone replacement materials, especially with health concerns regarding homologous bone grafts, which are associated with the risks of viral infections, such as Hepatitis B and Human Immune deficiency Virus. Consequently, there is an increasing interest in the development of synthetic bone replacement materials for the filling of both load bearing and non-load bearing osseous defects, such as in joint and facial reconstruction, with a resulting expansion in this field of research.

The biocompatibility of hydroxyapatite (HA), coupled with the similarities between the crystal structure of HA and the mineral content of bone, has led to great interest in HA as a material for the augmentation of osseous defects. The apatite group of minerals are based on calcium phosphate, with stoichiometric hydroxyapatite having a molar ratio of Ca/P of 1.67. HA has the chemical formula $Ca_{10}(PO_4)_6(OH)_2$. There has also been increasing interest in the development of biomaterials, such as bioactive glasses and substituted apatites, which more closely match the chemical composition of bone mineral, resulting in faster bone bonding between implant and host. However, as a result of the poor mechanical properties of all of these materials, clinical usage has been limited to coatings and non-load bearing porous structures or granules.

Porous bio-ceramic implants offer the potential of tailored-skeletal repair and reconstruction in a variety of orthopaedic procedures, as well as secure fixation of the implant as a result of bony ingrowth and mechanical interlock. There are a number of porous HA based implant materials currently available on the commercial market, for example Unilab, Surgibone, Endobon®, Ceros, Interpore. Many of these materials are derived from either animal cancellous bone or coral, which is hydrothermally treated so as to convert the natural ceramic component into hydroxyapatite, while preserving the natural porous structure. For example, Endobon® is produced via the hydrothermal conversion of bovine cancellous bone. Others are formed by conventional burn-out routes, wherein polymer beads dispersed throughout a ceramic structure are burnt out to leave a foam-like structure. This procedure generates significant gaseous by-products and often results in cracking of the structure.

There is limited information and control on the physical characteristics, such as the modal macro-pore size or the degree of pore inter-connectivity, in many of these porous structures, and in some cases there is limited control over the chemical composition. Both the physical and chemical properties influence the quality and rate of bone ingrowth within these materials on implantation. Furthermore, the mechanical properties are highly sensitive to both density- and anisotropy-parameters, which again are not well controlled in many of the current production routes. Therefore, there is a need for the development of a novel production route which allows control of the physical and chemical properties of the final product. This results in improved implants in terms of mechanical and biological performance, as a function of tailored properties and improved reproducibility.

Ceramic foams are conventionally formed by infiltrating a polymer foam with a slip, which is a fine slurry of ceramic particles in a fluid, such as water. When the aggregate is fired, the slip bonds to the polymer foam to give an image of the original foam, which is burnt off. Ceramic foams may also be made by chemical vapour deposition on to a substrate of reticulated carbon foam.

The present invention aims to provide a method for the manufacture of porous materials with highly interconnected porosity, which are suitable for use in medical applications.

Accordingly, the present invention provides a method for the production of a macroporous ceramic foam, which method comprises:
(a) forming a ceramic slip comprising a substantially homogeneous mixture of a ceramic particulate, an organic binder in a liquid carrier and optionally one or more surfactants, wherein at least one surfactant is present if the organic binder does not function as a surfactant, and wherein the ceramic slip preferably has a viscosity in the range of from 15 to 200 $mPas^{-1}$;
(b) foaming the ceramic slip; and
(c) heating the foamed ceramic slip at a temperature sufficient to substantially burn out the organic binder.

For the avoidance of doubt, by the term macroporous, as applied to an open foam structure, is meant a ceramic foam containing pores with a modal diameter $d_{mode} \geq 100$ μm. By the term microporous, as applied to the porosity within the struts of the ceramic foam, is meant containing pores with a modal diameter $0.1$ μm $\leq d_{mode} \leq 50$ μm.

Foams are three-dimensional cellular solids and may be classified as either open-celled or closed-cell. The relative density of a cellular material is defined as the ratio of the density of the cellular material to that of the solid material. For bone, the relative density generally falls within the range of from 0.05 to 0.7, i.e. 30 to 95% porous. Furthermore, determination of the relative density of a porous structure can give an indication of the degree of pore connectivity with the structure. For cancellous bone, a structure with a relative density of less than approximately 0.2 (i.e. 80% porous) is generally classed as open, while one with a relative density of more than approximately 0.2 (i.e. 80% porous) will possess a closed (non-interconnected) porosity.

The ceramic slip preferably has a viscosity in the range of from 15 to 200 $mPas^{-1}$, more preferably from 30 to 100 $mPas^{-1}$. It has been found that the viscosity of the slip is important for producing a stable foam, prior to burning out the binder. The presence of a surfactant in the slip also assists in producing a stable foam. It will be appreciated that if the binder is capable itself of acting to a sufficient extent as a surfactant, then the optional surfactant(s) may be dispensed with. Suitable examples of surfactants for use in the present invention include Saponin and Decon 90.

The ceramic particulate may be a biocompatible ceramic and may comprise, for example, one or more of hydroxyapatite, a substituted-hydroxyapatite and/or alumina, or any other ceramic used in biomedical applications. The ceramic particulate may also comprise a glass or a glass-ceramic such as, for example, an AW-Glass ceramic. The ceramic particulate may preferably be either a spray dried and/or calcined powder, or, advantageously, it may be directly obtained from the as-precipitated filter cake.

In general, the ceramic particulate has a particle size distribution with the following characteristics: $d_{10}$ from 0.5 to 20, preferably from 0.5 to 5 µm, more preferably from 1 to 15 µm, still more preferably from 0.7 to 2.5 µm, still more preferably from 0.9 to 2.1 µm; $d_{50}$ from 1 to 300 µm, preferably from 2 to 150 µm, more preferably from 1 to 15 µm, still more preferably from 1 to 10 µm, still more preferably from 3 to 8 µm; and a $d_{90}$ of from 0.5 to 150 µm, preferably from 5 to 50 µm, more preferably from 10 to 50 µm, still more preferably from 10 to 40 mm, still more preferably from 10 to 25 µm. The mode of the particle size will typically fall in the range of from 1 to 400 µm, preferably from 2 to 250 µm, more preferably from 1 to 10 µm, still more preferably from 3 to 6 µm. The ceramic particulate typically has a surface area of from 5 to 200 $m^2 g^{-1}$, preferably from 7 to 100 $m^2 g^{-1}$, more preferably from 7 to 20 $m^2 g^{-1}$, and still more preferably from 7 to 14 $m^2 g^{-1}$. Particle sizes were measured using a Malvern Mastersizer. Surface areas were measured using a Micromeretics B.E.T. Surface Analyser.

The organic binder serves to provide plasticity during forming of the ceramic particulate and green strength in the formed product. In the present invention, the organic binder preferably comprises an organic binder, which is preferably water soluble. Suitable examples include vinyl polymers, such as poly(vinyl alcohol), poly(vinyl pyrrolidone), poly(vinyl acetate) and/or poly(vinyl butyral). Other suitable examples include alginate, poly(lactic acid) and poly(ethylene glycol). It will, however, be appreciated that any polymeric species capable of providing mechanical stability to a pre-sintered ceramic foam body may be used. It will also be appreciated that the organic binders may be used singularly or in a combination of two or more thereof.

The liquid carrier should be one which can substantially dissolve the organic binder and which can also be combined with the ceramic powder without causing degradation thereof. Suitable examples include water, preferably double distilled water, alcohols, such as propan-2-ol, and hydrocarbons, such as trichloroethane. The organic binder will generally be present in the liquid carrier in an amount of from 0.2 to 10 w/v %, preferably from 0.2 to 8 w/v %, more preferably from 0.5 to 6 w/v %, still more preferably from 0.5 to 4 w/v %, still more preferably from 1.5 to 3 w/v %.

The ceramic slip preferably comprises in the range of from 10 to 95 w/v % ceramic particulate in the binder and liquid carrier, more preferably from 20 to 90 w/v % ceramic particulate in the binder and liquid carrier, still more preferably from 40 to 80 w/v % ceramic particulate in the binder and liquid carrier. The slip may suitably be prepared by combining the constituents into a homogenous mixture. The concentration of the binder solution added should preferably be selected to ensure that the percentage of binder remaining in a dry casting is in the range of form 0.5 to 10 w/w %, preferably from 1 to 6 w/w %, more preferably from 1 to 4 w/w %. The final slip should preferably have a viscosity in the range of from 15 to 200 $mPas^{-1}$, more preferably from 30 to 100 $mPas^{-1}$, and this may be achieved by adjusting the slip viscosity by the addition of extra solvent, as necessary.

The ceramic slip may further comprise one or both of a dispersant and/or a defloculant. Suitable examples include sodium polyacrylate and/or sodium hexameta phosphate.

Foaming of the ceramic slip may be achieved by one or more of mechanical agitation, gassing and/or the use of a blowing agent, such as $H_2O_2$. For example, foaming may be achieved by the use of a mechanical whisk and/or passing a gaseous phase through the slip until a substantially stable homogenous foam has been produced. Advantageously, foaming is achieved by the use of a ball mill (mill-foaming). Suitable milling media includes alumina ($Al_2O_3$), enstatite ($MgSiO_3$) or zirconia ($ZrO_2$) balls, preferably having a diameter in the range of from 10 to 30 mm, more preferably from 15 to 25 mm. For biomedical applications, the milling media should be chosen carefully so as to avoid contamination of the slip. The ball mill may be used in conjunction with gassing and/or a blowing agent. The amount of milling media to be used when mill-foaming a ceramic slip is advantageously in the range of from 3 to 20 w/w % ceramic particulate to milling media, more preferably from 5 to 15 w/w %.

There are a number of advantages associated with ball milling foam-stabilised slips, including:—

(i) No organic sponge/foam template or solid pore-formers to burnout; porous ceramics produced by burnout methods often have relatively low mechanical properties resulting from defects in the structure due to incomplete/irregular burn-out of the original template.

(ii) Homogeneous or functionally graduated pore distributions are attainable by varying the slip viscosity.

(iii) Macro-pore size is variable by varying the start-powder particle size.

(iv) Macro-porosity is highly interconnected.

(v) Microstructure contains an interconnected network of micro-pores, the degree of connectivity of which can be controlled during sintering. This is important for tailoring the drug delivery characteristics of the porous structure.

Prior to burn-out of the organic binder, the liquid carrier is preferably allowed to evaporate from the foamed ceramic slip. This is beneficial because excessive quantities of the liquid carrier can lead to cracking during the subsequent heat-treatment steps. Evaporation may be facilitated by heating the foamed ceramic slip to a temperature in the range of from 20 to 100° C., preferably 30 to 50° C., and preferably with a flow of air thereover. As already mentioned, the concentration of the organic binder in the liquid carrier is advantageously selected so that the percentage of binder remaining after substantially all of the liquid carrier has been evaporated is in the range of from 0.5 to 10 w/w %, preferably from 1 to 6 w/w % more preferably from 1 to 4 w/w %, since this has been found to reduce the occurrence of cracking during the subsequent heat-treatment steps. The viscosity of the slip and the presence of a surfactant/stabilizer assist in maintaining the foam structure of the ceramic slip during evaporation of the liquid carrier. In other words, the collapse of the form structure is delayed.

The foamed ceramic slip will generally be cast in a mould prior to burn-out of the organic binder. The mould preferably has a surface coated with a release agent to ensure release of the casting(s) after removal of the liquid carrier has occurred. The foamed ceramic slip may also be cast (unconstrained) on a flat surface, preferably dusted with a fine ceramic powder. Injection of the foamed ceramic slip into a porous mould is also possible.

It will be appreciated that the burn-out temperature will depend upon the nature of the organic binder. Generally the burn-out temperature will fall in the range of from 150 to 700° C., preferably 300 to 700° C., more preferably 300 to 600° C. Burn-out should preferably be carried out slowly in order to avoid creation of pressures due to decomposition of the organic binder and evaporation of any residual moisture. Sufficient amounts of oxygen or air should preferably be supplied so that substantially complete binder burn-out can occur, and binder burn-out is therefore advantageously carried out in a ventilated furnace. Heating of the foamed ceramic slip is carried our at a rate and temperature sufficient to substantially burn-out the organic binder.

Following burn-out of the organic binder, the ceramic foam may be sintered, again advantageously in a ventilated furnace. The sintering temperature depends upon the nature of the ceramic particulate and will typically fall in the range of from 500 to 1600° C. It will be appreciated that the sintering temperature and atmosphere must be chosen carefully to avoid decomposition of the ceramic material. After burn-out, humid, $CO_2$-rich atmospheres may be required for some ceramics, for example carbonate-substituted apatites. In particular, for carbonate-substituted apatite foams, specimens are preferably sintered at a temperature in the range of from 600 to 1000° C. under a carbon dioxide atmosphere, preferably in a tube furnace or the like, which is constantly flushed with $CO_2$ gas at a flow rate of typically up to 4 $lmin^{-1}$, preferably from 1 to 3 $lmin^{-1}$, more preferably approximately 2.0 $lmin^{-1}$.

In a preferred embodiment of the present invention, following evaporation of the liquid carrier, the substantially dry green castings may undergo a stepped heat-treatment for binder burn-out and densification by sintering. The optimum parameters for the burn-out step will depend on the binder being used. However, castings are typically heated at a rate of from 0.5 to 10° C. $min^{-1}$ (preferably from 1 to 5° C. $min^{-1}$) and held at a burn-out temperature of from 150 to 700° C. (preferably from 300 to 700° C.) for from 2 to 8 hours. During the burn-out stage it is recommended that air is passed through the furnace at a flow rate of preferably from 0.5 to 2 $lmin^{-1}$, more preferably from 1 to 2 $lmin^{-1}$, to ensure substantial removal of the binder. Once burn-out of the binder is complete, castings may be heated directly from the burn-out temperature, at a rate typically from 1 to 20° C. $min^{-1}$, to a sintering temperature appropriate for the ceramic powder, typically from 500 to 1600° C. Alternatively, castings that have undergone burn-out may be cooled to room temperature and then sintered. Upon sintering, it has been found that the struts of the material may typically densify to from approximately 60 to ≥95% (more typically from 70 to ≥90%) of the theoretical density. On cooling, the sintered bodies are removed from the furnace and may be sectioned using a diamond tipped cutting apparatus into the desired geometry. The resulting solid foamed ceramic material may be provided in the form of, for example, blocks, cylinders and granules.

The foamed ceramic material produced by the method according to the present invention may be used as a synthetic bone material, including dental materials, for example for use in bone reconstruction and augmentation, implants, and compaction graft-type fillers and for making hydroxyapatite-polymer composites.

The final macro-structure of the sintered ceramic foams produced according to the method of the present invention may be controlled by varying the relative proportions of the ingredients within the ceramic slip, the physical characteristics of the ceramic particulate and the amount of milling media added during mill-foaming, within the limits specified. Hence, the bulk porosities of ceramic foams produced via this method typically range from 40 to 95% (more typically from 60 to 90%, still more typically from 60 to 80%, still more typically from 70 to 80%). The macro-porosity of the sintered ceramic foams produced according to the method of the present invention are highly interconnected (as can be seen in FIGS. 1 to 3). Furthermore, modal macro-pore size varies with bulk porosity, and ranges from 100 to 2000 μm, more typically from 100 to 1000 μm (as can be seen in FIGS. 7 and 8).

The final micro-structure of the sintered ceramic foams produced according to the method of the present invention may be controlled by varying the relative proportions of the ingredients within the ceramic slip, the physical characteristics of the ceramic particulate, the amount of milling media added during mill-foaming and, additionally by the sintering procedure, within the limits specified. The strut density (or real density) typically ranges from 60 to 95% (more typically from 70 to 95%, still more typically from 85 to 92%) of the theoretical density of the ceramic (the theoretical density of hydroxyapatite is 3.156 $gcm^{-3}$). However, the micro-porosity of the sintered ceramic foams produced according to the method of the present invention are highly interconnected (as can be seen in FIGS. 4 to 6 and 9 and 10) a characteristic of particular significance for biomedical application. Furthermore, the degree of interconnectivity within the microstructure of the sintered ceramic foams produced according to the method of the present invention, may be controlled by varying the relative proportions of the ingredients within the ceramic slip, the physical characteristics of the ceramic particulate, the amount of milling media added during mill-foaming and, additionally by the sintering procedure.

$$\text{Real (or Strut) Density} = \frac{\text{Mineralised Mass}}{\text{Volume of Bone Struts}}$$

$$\text{Apparent (or Bulk) Density} = \frac{\text{Mineralised Mass}}{\text{Total (pore + strut) Volume}}$$

$$\text{Bulk Porosity (\%)} = 100 \times \left(1 - \frac{\text{Apparent Density}}{\text{Theoretical Density}}\right)$$

$$\text{Apparent Density} = \frac{\text{Dry Weight} \times \text{Density of Water}}{\text{(Saturated weight} - \text{Submerged weight)}}$$

$$\text{Real Density} = \frac{\text{Dry Weight} \times \text{Density of Water}}{\text{(Dry weight} - \text{Submerged weight)}}$$

The present invention will now be described further with reference to the following Examples and Figures, provided by way of example, in which:

FIG. 1 is a SEM micrograph of a sintered mill-foamed porous ceramic material according to Example 1 of the present invention (sintering temperature 1200° C., magnification ×50)

FIG. 2 is a SEM micrograph of a sintered mill-foamed porous ceramic material according to Example 1 of the present invention (sintering temperature 1300° C., magnification ×50)

FIG. 3 is a SEM micrograph of a sintered mill-foamed porous ceramic material according to Example 1 of the present invention (sintering temperature 1400° C., magnification ×1000)

FIG. 4 is a SEM micrograph of a sintered mill-foamed porous ceramic material according to Example 1 of the present invention (sintering temperature 1200° C., magnification ×1000) (Ref: TAG 396).

FIG. 5 is a SEM micrograph of a sintered mill-foamed porous ceramic material according to Example 1 of the present invention (sintering temperature 1300° C., magnification ×1000)

FIG. 6 is a SEM micrograph of a sintered mill-foamed porous ceramic material according to Example 1 of the present invention (sintering temperature 1400° C., magnification ×50)

FIG. 7 is a SEM micrograph of a sintered mill-foamed porous ceramic material according to Example 4 of the present invention (55 w/v % particulate to carrier, magnification ×50)

FIG. 8 is a SEM micrograph of a sintered mill-foamed porous ceramic material according to Example 4 of the present invention (50 w/v % particulate to carrier, magnification ×50)

FIG. 9 is a SEM micrograph of a sintered mill-foamed porous ceramic material according to Example 4 of the present invention (55 w/v % particulate to carrier, magnification ×1000)

FIG. 10 is a SEM micrograph of a sintered mill-foamed porous ceramic material according to Example 4 of the present invention (50 w/v % particulate to carrier, magnification ×1000)

FIG. 11 is a plot of bulk and strut densities of sintered mill-foamed porous ceramics prepared according to Example 1 of the present invention

EXAMPLE 1

3.0 g of polyvinyl alcohol (molecular weight 115000) was dissolved in 170 ml of double distilled water at 40° C., under conditions of continuous stirring. This binder solution was then combined with 100 g of hydroxyapatite powder with a particle $d_{50}$ of 3.3 μm and a surface area of 13.4 $m^2 g^{-1}$. The resulting slip was then placed in a 1 liter mill pot with 945 g of milling media (18 mm diameter alumina balls) and milled at a speed of 120 rpm for 2 hours. The thus foamed slip was then cast on to a flat surface which had been dusted with a fine hydroxyapatite powder, equivalent to 0.1 $gcm^{-2}$ mould area, to ensure release of the casting once dry. Castings were dried in air at a temperature of 40° C. for from 12 to 24 hours. The dried green castings underwent a stepped heat treatment in a ventilated furnace for binder burn-out and densification by sintering. Castings were heated at a rate of 2.5° C. $min^{-1}$ to 500° C., and held at this temperature for 4 hours. Upon burn-out the castings were then heated at a rate of 2.5° C. $min^{-1}$ to temperatures of 1200, 1300 and 1400° C., with no air flow and held for 2 hours. FIGS. 1 to 6 are SEM micrographs of the thus formed materials: FIG. 1 (sintering temperature 1200° C., magnification ×50), FIG. 2 (sintering temperature 1300° C., magnification ×50), FIG. 3 (sintering temperature 1400° C., magnification ×1000), FIG. 4 (sintering temperature 1200° C., magnification ×1000), FIG. 5 (sintering temperature 1300° C., magnification ×1000), FIG. 6 (sintering temperature 1400° C., magnification ×50). The physical characteristics of the sintered specimens are detailed in FIG. 11. The theoretical density of hydroxyapatite is 3.156 $gcm^{-3}$.

The results demonstrate how variation of sintering temperature results in control of both the bulk and strut density. Bulk density increases steadily as sintering temperatures increases from 1200 to 1400° C., which reflects shrinkage of the macro-porosity, with a concurrent decrease in the macro-porous connectivity. However, strut density decreases from 1200 to 1400° C. as a result of a reduction in micro-pore connectivity leading to an increase in closed micropores.

EXAMPLE 2

Two slips were prepared as in Example 1. The slips were then each placed in a separate 1 liter mill pot with 630 and 945 g of milling media (18 mm diameter alumina balls) and milled as a speed of 120 rpm for 5 hours. The foamed slips were then cast on to a flat surface which had been dusted with a fine hydroxyapatite powder, equivalent to 0.1 $gcm^{-2}$ mould area, to ensure release of the casting once dry. Castings were dried at a temperature of 40° C. The dried green castings underwent a stepped heat treatment for binder burn-out and densification by sintering. Castings were heated at a rate of 2.5° C. $min^{-1}$ to 500° C., and held at this temperature for 4 hours. Upon burn-out the castings were then heated at 2.5° C. $min^{-1}$ to a temperature of 1300° C., and held for 2 hours. The physical characteristics of the sintered specimens are detailed in Table 1.

TABLE 1

| Weight of Milling Media (g) | Bulk Density ($gcm^{-3}$) | Strut Density ($gcm^{-3}$) |
|---|---|---|
| 630 | 0.65 | 2.75 |
| 945 | 0.54 | 2.74 |

The results in Table 1 demonstrate how variation in the weight of the milling media can be used to control of the bulk density (macro-porosity) independently of the strut density. Sintered mill-foamed porous ceramic prepared with a greater loading of milling media have a more open macro-porous structure.

EXAMPLE 3

3.0 g of polyvinyl alcohol (molecular weight 115000) was dissolved in 130 ml of double distilled water at 40° C., under conditions of continuous stirring. This binder solution was then combined with 100 g of hydroxyapatite powder with a particle $d_{50}$ of 7.5 μm and a surface area of 7.61 $m^2 g^{-1}$. The resulting slip was then placed in a 1 liter mill pot with 945 g of milling media (18 mm diameter alumina balls) and milled at a speed of 120 rpm for 5 hours. The foamed slip was then cast on to a flat surface which had been dusted with a fine hydroxyapatite powder, equivalent to 0.1 $gcm^2$ mould area, to ensure release of the casting once dry. Casting were dried at a temperature of 40° C. The dried green castings underwent a stepped heat treatment for binder burn-out and densification by sintering. Casting were heated at a rate of 2.5° C. $min^{-1}$ to 500° C., and held at this temperature for 4 hours. Upon burn-out, the castings were then heated at 2.5° C. $min^{-1}$ to a temperature of 1300° C. and held at this temperature for 2 hours. The physical characteristics of the sintered specimens are detailed in Table 2.

TABLE 2

| Bulk Density ($gcm^{-3}$) | Strut Density ($gcm^{-3}$) |
|---|---|
| 0.35 | 2.42 |

The results in Table 1, compared with the results of the sintered mill-foamed porous ceramics prepared with 945 g milling media in Table 2, demonstrate how variation in the particle size of the ceramic particulate may be used to control the bulk density (macro-porosity) and the strut density (micro-porosity). The sintered mill-foamed porous ceramics prepared with the ceramic particulate possessing a larger particle size had a greater modal pore size of 800 μm as compared to 300 μm.

EXAMPLE 4

2.0 g of polyvinyl alcohol (molecular weight 115000) was dissolved in 90 ml of double distilled water at 40° C., under conditions of continuous stirring. 2.0 g of polyvinyl alcohol (molecular weight 115000) was dissolved in 100 ml of double distilled water at 40° C., under conditions of continuous stirring. These binder solutions were then each combined with 50 g of powdered hydroxyapatite filter-cake with a particle $d_{50}$ of 40 μm and a surface area of 78 $m^2 \cdot g^{-1}$. The resulting slips were then each placed in a 1 liter mill pot with 450 g of milling media and milled at a speed of 120 rpm for 2 hours. The foamed slips were then cast on to a flat surface which had been dusted with sufficient fine hydroxyapatite powder, equivalent to 0.1 g per cm² mould area, to ensure release of the casting once dry. Castings were dried at a temperature of 40° C. The dried green castings underwent a stepped heat treatment for binder burn-out and densification by sintering. Castings were heated at a rate of 1.0° C. min$^{-1}$ to 500° C., and held at temperature for 4 hours. Upon burnout the castings were then heated to a temperature of 1250° C., and held at temperature for 2 hours. The physical characteristics of the sintered specimens are illustrated in FIGS. 7 to 10 and are detailed in Table 3.

TABLE 3

| Liquid Carrier (ml) | Bulk Density (g · cm$^{-3}$) | Strut Density (g · cm$^{-3}$) |
|---|---|---|
| 90 | 0.84 | 2.77 |
| 100 | 0.41 | 2.39 |

The results in Table 3 and FIGS. 7 to 10 demonstrate how variation in the ratio of ceramic particulate to binder solution results in variation in both the bulk density (macro-porosity) and the strut density (micro-porosity). The sintered mill-foamed porous ceramics prepared with the greater volume of liquid carrier have lower bulk and strut densities reflecting a more open, inter-connected pore structure with larger macro-pores and a larger fraction of micro-porosity. Furthermore, the use of powdered filter-cake has resulted in a more organised network of inter-connected microporosity.

The macroporous ceramic foams according to the present invention have the following advantages over the prior art cancellous and coral derived materials. First, the synthetic source means that there is total control over the choice of phase composition and the level of chemical purity. Second, the processing route enables substantially complete control of the pore structure so as to minimise batch variation. Third, substantially isotropic structures can be produced. Fourth, the processing route enables the structural features (such as the pore size and connectivity) of both the macro-porosity and micro-porosity to be tailored to the specific application so that structural and mechanical properties may be matched to particular requirements.

The invention claimed is:

1. A method of producing a macroporous sintered ceramic foam biomedical bone structure, which method comprises:
   (a) forming a ceramic slip comprising a substantially homogeneous mixture of a ceramic particulate, an organic binder in a liquid carrier, and optionally one or more surfactants, wherein at least one surfactant is present if the organic binder does not function as a surfactant
   (b) foaming the ceramic slip using a ball mill;
   (c) heating the foamed ceramic slip at a temperature sufficient to substantially burn out the organic binder; and
   (d) sintering the foamed ceramic slip following burn out of the organic binder thereby forming said macroporous sintered ceramic foam biomedical bone structure consisting of a homogenous open foam structure containing pores with a modal diameter $d_{mode}$ of from 100 μm to 1000 μm and a bulk porosity of from 40 to 95%.

2. A method as claimed in claim, 1, wherein foaming of the ceramic slip is achieved using a ball mill with milling media selected from alumina ($Al_2O_3$), enstatite ($MgSiO_3$) or zirconia ($ZrO_2$) balls.

3. A method as claimed in claim 2, wherein the balls of the milling media have a diameter in the range of from 10 to 30 mm.

4. A method as claimed in claim 2, wherein the balls of the milling media have a diameter in the range of from 15 to 25 mm.

5. A method as claimed in claim 1, wherein foaming of the ceramic clip is achieved using a ball mill in conjunction with gassing and/or a blowing agent.

6. A method as claimed in claim 1, wherein the ceramic slip has a viscosity in the range of from 30 to 100 mPas.

7. A method as claimed in claim 1, wherein the ceramic particulate is biocompatible.

8. A method as claimed in claim 1, wherein the ceramic particulate comprises one or more of hydroxyapatite, a substituted-hydroxyapatite, a glass, an AW-glass ceramic and/or alumina.

9. A method as claimed in claim 1, wherein the ceramic particulate has a $d_{50}$ of from 1 to 300 μm.

10. A method as claimed in claim 1, wherein the ceramic particulate has a surface area in the range of from 5 to 200 m² g$^{-1}$.

11. A method as claimed in claim 1, wherein the organic binder comprises one or more of poly (vinyl alcohol), poly (vinyl pyrrolidone), alginate, poly (lactic acid), poly (vinyl butyral), poly (ethylene glycol) and/or poly (vinyl acetate).

12. A method as claimed in claim 1, wherein the liquid carrier comprises water, propan-2-ol or trichloroethane.

13. A method as claimed in claim 1, wherein the organic binder is present in the liquid carrier in an amount of from 0.2 to 10 w/v %.

14. A method as claimed in claim 13, wherein the organic binder is present in the liquid carrier in an amount of from 0.5 to 6 w/v %.

15. A method as claimed in claim 13, wherein the organic binder is present in the liquid carrier in an amount of from 0.5 to 4 w/v %.

16. A method as claimed in claim 1, wherein the ceramic slip comprises from 10 to 95 w/v % ceramic particulate.

17. A method as claimed in claim 16, wherein the ceramic slip comprises from 20 to 90 w/v % ceramic particulate.

18. A method as claimed in claim 16, wherein the ceramic slip comprises from 40 to 80 w/v % ceramic particulate.

19. A method as claimed in claim 1, wherein the ceramic slip further comprises one or both of a dispersant and/or a defloculant.

20. A method as claimed in claim 1, wherein prior to burn-out of the organic binder the liquid carrier is allowed to evaporate from the foamed carrier slip.

21. A method as claimed in claim 20, wherein the foamed ceramic slip is heated at a temperature in the range of from 20 to 100° C. to facilitate evaporation of the liquid carrier prior to burn-out of the organic binder.

22. A method as claimed in claim 20, wherein the concentration of the organic binder in the liquid carrier is selected such that the percentage of binder remaining after substantially all of the liquid carrier has been evaporated is from 0.5 to 10 w/w %.

23. A method as claimed in claim 22, wherein the concentration of the organic binder in the liquid carrier is selected such that the percentage of binder remaining after substantially all of the liquid carrier has been evaporated is in the range of from 1 to 6 w/w %.

24. A method as claimed in claim 22, wherein the concentration of the organic binder in the liquid carrier is selected such that the percentage of binder remaining after substantially all of the liquid carrier has been evaporated is in the range of from 1 to 4 w/w %.

25. A method as claimed in claim 1, wherein the foamed ceramic slip is cast in a mould having a surface coated with a release agent.

26. A method as claimed in claim 1, wherein burn-out of the organic binder is carried out at a temperature in the range of from 150 to 700° C.

27. A method as claimed in claim 1, wherein sintering is carried out at a temperature in the range of from 500 to 1600° C.

28. A method as claimed in claim 1, wherein the sintered ceramic foam has a strut density in the range of from 60 to 95%.

29. A method as claimed in claim 1, wherein the ceramic particulate has a $d_{50}$ of from 1 to 15 μm.

30. A method as claimed in claim 1, wherein the sintered ceramic foam has a bulk porosity in the range of from 70 to 90%.

31. A method as claimed in claim 1, wherein the sintered ceramic foam has a strut density in the range of from 70 to 90% of the theoretical density of the ceramic.

* * * * *